US00PP25351P2

(12) United States Plant Patent
Horvath

(10) Patent No.: US PP25,351 P2
(45) Date of Patent: Mar. 17, 2015

(54) ***GEUM* PLANT NAMED 'BANANA DAIQUIRI'**

(50) Latin Name: ***Geum* hybrid**
Varietal Denomination: Banana Daiquiri

(76) Inventor: Brent Horvath, Fontana, WI (US)

( * ) Notice: Subject to any disclaimer, the term of this patent is extended or adjusted under 35 U.S.C. 154(b) by 216 days.

(21) Appl. No.: 13/573,216

(22) Filed: Aug. 31, 2012

(51) Int. Cl.
*A01H 5/00* (2006.01)

(52) U.S. Cl.
USPC ..... Plt./263.1

(58) Field of Classification Search
CPC ..... A01H 5/00; A01H 5/02
USPC ..... Plt./263.1
See application file for complete search history.

*Primary Examiner* — June Hwu
*Assistant Examiner* — Louanne Krawczewicz Myer

(57) ABSTRACT

A new, distinct *Geum* plant as shown and described, characterized by ruffled semi double to single yellow flowers.

1 Drawing Sheet

Latin name: *Geum* hybrid.
Cultivar name: 'Banana Daiquiri'.

BACKGROUND OF THE INVENTION

The present invention relates to a new and distinct hybrid of *Geum* plant named 'Banana Daiquiri' characterized by ruffled semi double to single yellow flowers. The new *Geum* was the result of a breeding program in Hebron, Ill. since 2006. T he selection of the new plant was made in 2009 and was due to its' ruffled semi double to single yellow flowers. The initial asexual propagation of the new *Geum* plant was by division and took place at a nursery in Hebron, Ill. since 2009. Continued asexual propagation by division since that time has shown that the unique features of the new Geum plant are stable and reproduced true to type in successive generations.

SUMMARY OF THE INVENTION

In the following description, color references are made to The Royal Horticultural Society Colour Chart (2001). The new *Geum* plant named 'Banana Daiquiri' characterized by semi double to single flowers of yellow RHS 3B have been observed to be unique and stable.

Plants of the new *Geum* can be compared to Geum 'Tequila Sunrise' U.S. Pat. No. 21,514, patented. 1. The new plant flower color is yellow RHS 3B while Geum 'Tequila Sunrise' has a bicolor flower of yellow RHS 9B blending into 46A.

Plants of the new *Geum* can also be compared to *Geum* 'Diane' not patented. 1. The new plant flower color is lemon yellow RHS 3B while Geum 'Diane' has a flower color of golden yellow close to RHS 16 A. 2. The new plant also has flowers that are mostly semi double while *Geum* 'Diane' has a single flower.

DESCRIPTION OF PHOTOGRAPHS

Figure 1:
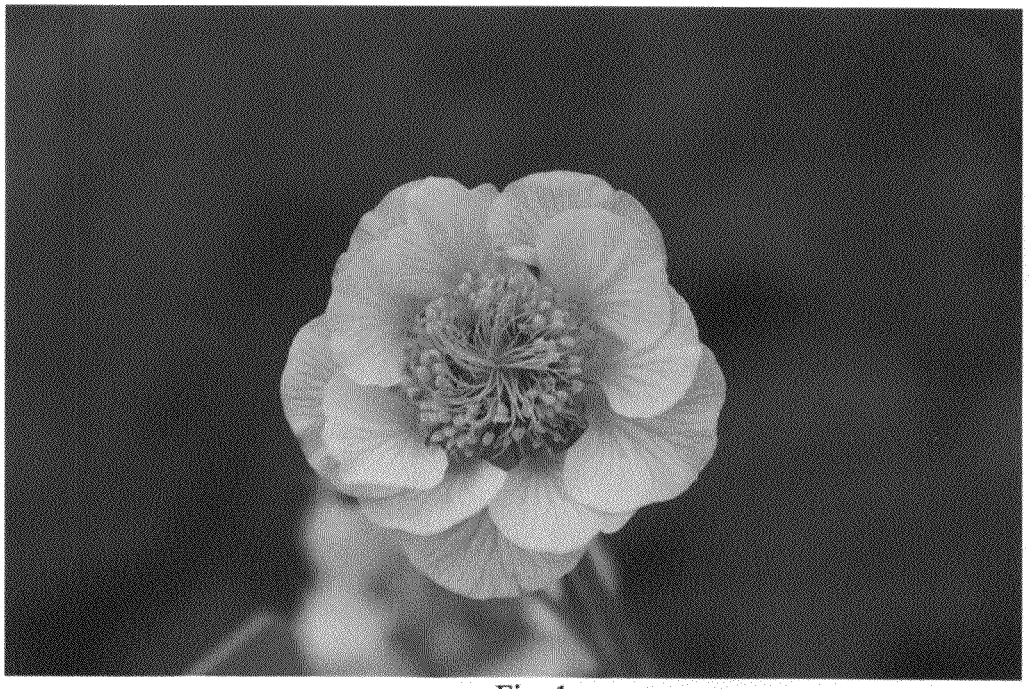
Figure 2:
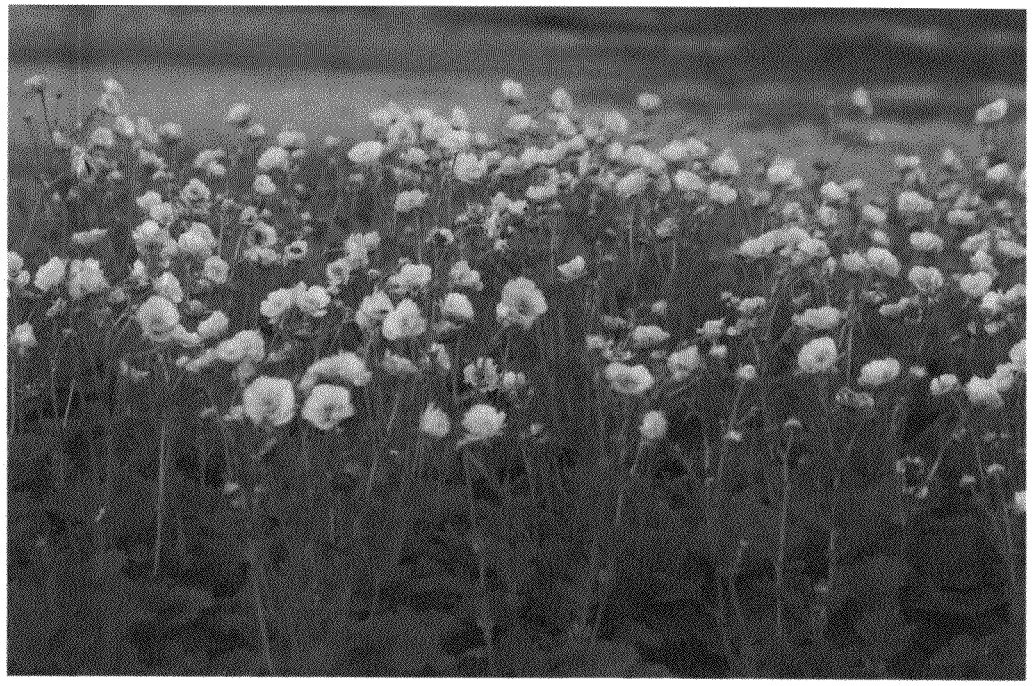

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 1 gallon container for one year at a nursery in Hebron, Ill. Measurements and numerical values represent averages of typical plants.

Botanical classification: *Geum* hybrid cultivar 'Banana Daiquiri'.

Parentage: Unknown.

Propagation: Vegetative division.

Plant description: Overall habit of the new *Geum* is basal clumps, with upright green flower stems topped by semi double to single flowers of a yellow color RHS 3B.

*Plant height.*—36 cm.
*Plant width.*—25-30 cm.
*Stem: diameter.*—3 mm.
*Stem or basal branches.*—Length up to 36 cm, with the internodes between basal foliage and first leaflet length being 7 cm and the second internodes between the first leaflet and the second leaflet length being 9 cm and the third. internodes between the second and third leaflet length being 7-8 cm.
*Stem coloration.*—Of the whole stem is RHS 144B.

Foliage description:

*Type.*—Herbaceous.
*Arrangement.*—Basal alternate with typically two or three lateral leaflets per stem.
*Petiole.*—Up to 12 cm long, with a diameter of 2 mm, color is 144B.
*Terminal leaflet length.*—Typically 15 mm.
*Terminal leaflet width.*—Typically 15 mm.
*Terminal leaflet shape.*—Obovate with incised margins.
*Terminal and lateral leaf apex.*—Acute.
*Terminal and lateral leaf base.*—Cuneate.
*Terminal and lateral leaf margin.*—Incised.
*Texture.*—Terminal and lateral leaf; upper and lower surfaces: pubescent.
*Venation pattern.*—Terminal and lateral leaf, upper and lower surfaces: pinnate.
*Venation color.*—Terminal and lateral leaf, upper surface is color 137 B and lower surface color is 137 C.
*Lateral leaflet number.*—2 or 3 per stem.
*Lateral leaflet length.*—2-3 cm.
*Lateral leaflet width.*—Up to 2 cm.
*Lateral leaflet shape.*—Obovate.
*Adaxial leaf description.*—Color is 146 A.
*Abaxial leaf description.*—Color 138 B.

Flower description:

*Flower type*.—Corymb.

*Adaxial flower color*.—3 B.

*Abaxial flower color*.—4 B.

*Flower size*.—Diameter: 25-30 mm across, depth 10-15 mm.

*Flower number*.—4-5 per stem, 90-135 per plant.

*Number flowering stems*.—20-30.

*Bloom period and duration*.—Beginning the first week of May into the first week of June in Hebron, Ill.

*Flower longevity and duration on the plant*.—Approximately 3-4 weeks.

*Flower longevity and duration cut*.—Approximately 5-7 days.

*Scent*.—None.

*Petal count*.—10-20.

*Petal shape*.—Spathulate.

*Petal arrangement*.—Rotate, overlapping.

*Petal diameter or width*.—12 mm across and petal length — 10 mm long.

*Petal apex*.—Retuse, base: attenuate, margin: entire.

*Petal texture*.—Upper and lower surfaces: smooth, glabrous.

*Petal color*.—Upper surface is color 3 B.

*Petal color*.—Lower surface color is 4 B.

*Petal venation*.—Type — reniform, vein color — upper surface close to 7A, Lower surface close to 7 B.

*Inflorescence diameter and height*.—8-12 cm across, 10 cm long.

*Flower buds*.—Diameter: 10-12 mm across, depth: 10 mm, shape: ovoid, surface: slightly pubescent and color between 59A and 59B.

*Sepal size*.—Length: up to 14 mm, diameter 6 mm at base coming to a point.

*Sepal quantity*.—6.

*Sepal shape*.—Lanceolate, apex: acute, base: cuneate, margin: entire.

*Sepal texture*.—Upper and lower surfaces: Pubescent.

*Sepal color*.—Adaxial color 59 A. Abaxial color 59 A.

*Peduncle color*.—144 B.

*Peduncle size*.—Length: 20-25 cm, diameter: 3 mm.

*Pedicel size*.—Length: 4-8 cm, diameter: 1-2 mm and color 144 B.

*Reproductive organs*.—Stamen — quantity over 100, length 1 cm.

*Anther*.—Quantity: over 100, length: 1 mm, diameter: close to 0.5 mm

*Pollen*.—Typically present, color: 12A.

*Stigma*.—None observed.

*Style*.—Number: over 50, length: 6 mm.

*Pistil*.—Number: over 50, length: 6+ mm.

*Ovaries*.—None observed.

*Fruit*.—None observed.

*Hardiness*.—USDA zone 4-8.

Disease resistance: Resistance to diseases common to *Geum* has not been observed on plants grown under nursery conditions.

I claim:

1. A new, distinct *Geum* plant as shown and described, characterized by ruffled semi double to single yellow flowers.

* * * * *